United States Patent [19]

Xanthopoulos

[11] 4,187,057
[45] Feb. 5, 1980

[54] PERISTALTIC INFUSION PUMP AND DISPOSABLE CASSETTE FOR USE THEREWITH

[75] Inventor: Piritheous Xanthopoulos, Cupertino, Calif.

[73] Assignee: Stewart-Naumann Laboratories, Inc., Santa Clara, Calif.

[21] Appl. No.: 868,525

[22] Filed: Jan. 11, 1978

[51] Int. Cl.² .................. F04B 43/12; F04B 45/08; A61M 5/00

[52] U.S. Cl. .................. 417/63; 128/214 F; 417/477

[58] Field of Search .............. 417/474, 475, 476, 477, 417/63; 128/214 F, DIG. 12

[56] References Cited

U.S. PATENT DOCUMENTS

| | | | |
|---|---|---|---|
| 2,899,905 | 8/1959 | Becher | 417/476 X |
| 2,965,041 | 12/1960 | Clark | 417/477 X |
| 3,297,184 | 1/1967 | Andelin | 215/307 |
| 3,366,071 | 1/1968 | Dutler | 417/477 |
| 3,437,224 | 4/1969 | Williams | 215/307 |
| 3,597,124 | 8/1971 | Adams | 417/477 |
| 3,658,445 | 4/1972 | Pulman et al. | 417/474 |
| 3,809,498 | 5/1974 | Lewis et al. | 417/477 |
| 3,816,033 | 6/1974 | Fried et al. | 417/475 X |
| 3,875,970 | 4/1975 | Fitter | 417/477 X |
| 3,927,955 | 12/1975 | Spinosa et al. | 417/477 |

*Primary Examiner*—Richard E. Gluck
*Attorney, Agent, or Firm*—Flehr, Hohbach, Test, Albritton & Herbert

[57] ABSTRACT

A disposable cassette for use in a peristaltic infusion pump is disclosed herein and includes a continuous tubular arrangement which is adapted to pass intravenous fluids therethrough. The disposable cassette also includes a cassette body which fixedly supports a predetermined tubular section of this tubular arrangement in a readily accessible position from outside the body. A peristaltic infusion pump is also disclosed herein and includes a first arrangement for supporting the disposable cassette for movement between an inoperative position and a spaced apart operative position, and a second arrangement which cooperates with the accessible section of the continuous tubular arrangement when the cassette is in its operative position for peristaltically pumping fluid through the tubular arrangement.

14 Claims, 16 Drawing Figures

PERISTALTIC INFUSION PUMP AND DISPOSABLE CASSETTE FOR USE THEREWITH

BACKGROUND OF THE INVENTION

The present invention relates generally to infusion pumps for administering intravenous fluids and more particularly to a specific type of peristaltic infusion pump which utilizes a specifically designed disposable cassette.

Infusion pumps are being used increasingly to administer intravenous (IV) fluids in intensive and coronary care units, laboratory and delivery rooms, and neonatal and pediatric departments as a replacement for the traditional gravity flow system. There are a number of different types of infusion pumps ranging from the relatively simple syringe type to the more complicated piston and cylinder and peristaltic types. Inasmuch as the present invention relates only to peristaltic infusion pumps, the present discussion will be so limited.

There are presently a number of specifically different peristaltic type infusion pumps either on the market or in the prior art generally. Obviously, these particular types of pumps have in common the fact that each utilizes peristaltic action on a tube for moving the fluid through it. In a typical linear pump, a series of finger like projections sequentially advance and retract to move the fluid toward the patient. In a typical rotary type pump, a plurality of rollers which are attached to a rotating disc alternately squeeze and release a section of tubing to move the fluid towards the patient. As will be seen hereinafter, the present invention relates more to the rotary type of pump than the linear type.

One example of a previously suggested rotary type peristaltic infusion pump is disclosed in U.S. Pat. Nos. 3,927,955 (Spinosa), dated Dec. 23, 1975 and 3,841,799 (Spinosa), dated Oct. 15, 1974. Each of these patents discloses what is referred to as a medical cassette pump which includes a single, continuous fluid-carrying tube for delivery of fluid from a fluid dispensing bottle to the patient. A section of this tube is positioned within the cassette and against the base or bases of the cassette so as to define an arcuate path which is substantially greater than 180° and, in at least one embodiment, almost a full 360°. A plurality of rollers located within this arcuate path act upon the supported tubular section for peristaltically moving liquids therethrough.

The peristaltic pump described in the Spinosa patents does have one advantage over some peristaltic pumps in the prior art. Specifically, Spinosa states that his cassette may be assembled with the tube, and furnished as a unit, each unit constituting a complete disposable cassette. However, there are certain disadvantages with the particular pump disclosed in these patents. In the first place, Spinosa utilizes a single continuous tube. If the particular section of this tube subjected to the peristaltic action is to withstand the typical abuse it will be subjected to, it must be of relatively high quality. However, this could be relatively expensive compared to the overall costs of the cassette. On the other hand, it certainly does not seem wise to utilize a tube which cannot withstand the intended and expected abuse it should receive during its useful life in order to minimize cost. In the second place, it should be noted that this tube is not fixedly held in place as it enters what Spinosa calls his cassette and it is not fixedly held in place as it leaves the cassette. As a result, there is a tendency for the tube to creep in the direction of the moving pump head. This, in turn, can adversely affect the accuracy of the pump and can cause the tube to stretch out of shape. Moreover, it can actually cause the tube to separate from its fluid dispensing bottle.

Another type of peristaltic pump suggested by the prior art, actually made available in the prior art, is one which includes a short length of its flexible tubing anchored at its opposite ends to stationary holding blocks. The mid portion of this tubing which is referred to as a pump chamber is stretched taut around three cylindrical rollers arrayed in a triangle on a rotor plate. The pump chamber is of course connected at one end to a reservoir of fluid (an IV bottle) and at the other end to the patient. In operation, the pump chamber, that is the flexible tubing, is pinched shut where it bends sharply around the rollers, but the lumen remains open between rollers. When the rotor plate turns, the points of occlusion advance along the pump chamber tube, and the fluid between them is pushed to the outlet end of the tube, as fresh fluid is drawn from the reservoir into the inlet end. The flow rate through this pump chamber, i.e., through the tube, depends upon the diameter and elastic properties of the tube and on the speed of the motor turning the rotor plate. While the speed may be set with a control knob so that the flow rate can be varied, this is only provided to a limited degree and, in actuality, three or more different tubes are required to cover a flow rate range of between 0.33 and 650 cc/hr.

While the peristaltic pump just described will most likely not creep because its ends are tied down, it does have certain other disadvantages. For example, this particular pump does not utilize or suggest utilizing a separate cassette at all but rather connects the tubing directly to the pump apparatus. This can be quite cumbersome and, more important, it can possibly lead to improper assembly of the tube around the pump head. Moreover, because of the particular way the tubing is arranged around the pump head, it is susceptible to stretching which in turn results in a change in flow rate resulting in inaccuracies. Further, this particular type of pump relies on a number of tubes to give a relatively wide low rate range which, of course, is time consuming and complicated.

As will be seen hereinafter, the present invention is directed to a particular peristaltic infusion pump and a particular disposable cassette, including tubing, for use with the pump. As will also be seen, this overall pump assembly, which is constructed in accordance with the present invention, does not have the various disadvantages discussed above.

OBJECTS AND SUMMARY OF THE INVENTION

One object of the present invention is to provide a peristaltic infusion pump assembly including a pump and separate disposable cassette, which assembly is uncomplicated in design and reliable in use.

Another object of the present invention is to provide an assembly wherein the disposable cassette can be rapidly but reliably placed in its operating position within the assembly.

Still another object of the present invention is to reliably lock the cassette in place once located in its operating position.

Yet another object of the present invention is to provide the peristaltic infusion pump assembly including an uncomplicated and reliable peristaltic pump head.

A further object of the present invention is to provide an individual disposable cassette which is uncomplicated in design, economical to manufacture and easy to assemble but also which is reliable in use.

Still a further object of the present invention is to provide a cassette utilizing a tubular arrangement which can be economically provided without compromising quality.

Yet a further object of the present invention is to provide a disposable cassette which is designed to prevent its tubular arrangement from creeping or from being stretched or otherwise deformed.

Still a further object is to provide a disposable cassette which is designed for readily detecting air bubbles or the like in the tubular arrangement.

As stated previously, the peristaltic infusion pump constructed in accordance with the present invention includes a disposable cassette and pump arrangement. The cassette includes a continuous tubular arrangement which is adapted to pass intravenous liquids therethrough and a cassette body for fixedly supporting a predetermined tubular section of the tubular arrangement in a predetermined and readily accessible location. The pump arrangement includes means for supporting the disposable cassette for movement between a first inoperative position and a second spaced apart operative position and means cooperating with the predetermined tubular section of the disposable cassette when the latter is in its operative position for peristaltically pumping fluid through the tubular arrangement.

In a preferred embodiment, the tubular arrangement includes a flexible first tubular section, a second tubular section distinct from but joined with one end of the first section, and a third tubular section distinct from but joined with the other end of the first tubular section. The cassette body in this preferred embodiment includes an arcuate tube supporting surface having a predetermind radius of curvature, first means for fixedly supporting one end of the first tubular section in place adjacent one end of the tube supporting surface and second means for fixedly supporting the opposite end of the first tubular section in place adjacent the opposite end of the tube supporting surface. These first and second supporting means together fix an intermediate portion of the flexible first tubular section in place entirely across and in continuous contact with the tube supporting surface.

DETAILED DESCRIPTION AND PREFERRED EMBODIMENTS

Turning now to the drawings, wherein like components are designated by like reference numerals throughout the various figures, attention is first directed to FIG. 1 which illustrates a disposable cassette 10 constructed in accordance with the present invention and provided for use in a peristaltic infusion pump to be described hereinafter. This cassette includes a tubular arrangement which, in its preferred embodiment, is constructed of a plurality of distinct but connected sections. The cassette also includes a cassette body which reliably supports this tubular arrangement in position during operation of the overall peristaltic infusion pump assembly.

Figure 2:
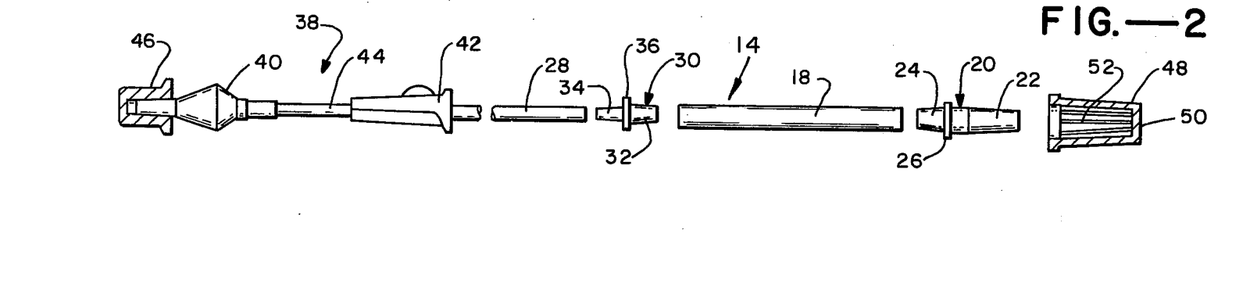
FIG. 2 is a plan view of a tubular arrangement comprising part of the cassette of FIG. 1.

Turning to FIG. 2, attention is specifically directed to tubular arrangement 14 which is shown unassembled for purposes of description. As seen in this figure, the arrangement includes a first tubular section 18 which, as will be seen hereinafter, is the only section to be subjected directly to peristaltic action. As a result, it is important that this section be of sufficiently high quality to withstand the abuse which normally accompanies continued peristaltic action. In a preferred embodiment of the present invention, this particular tubular section is between 0.100" and 0.200" in diameter (inner diameter), preferably 0.155" and constructed of medical grade silicone rubber tubing.

Arrangement 14 also includes a tubular section 20, specifically a conventional luer tip having a forwardmost end section 22 adapted for connection to external tubing (not shown). A reduced rearwardmost end section 24 of the tip is adapted for insertion into one end of tubular section 18 for connection therewith and an intermediate circumferential flange 26 separates the two end sections.

Arrangement 14 also includes a tubular section 28 which is distinct from section 18 and which is adapted for connection at one end to the otherwise free end of tubular section 18 by any suitable means, for example a conventional plastic connector 30. As illustrated in FIG. 2, tubular section 28 is smaller in diameter than previously described tubular section 18. For example, in an actual embodiment section 18 is 0.155" and section 28 is 0.118". Accordingly, connector 30 includes one end section 32 appropriately sized for insertion into the tubular section 18 and a substantially reduced opposite end section 34 for insertion into tubular section 28. A circumferential flange 36 separates these two end sections. Inasmuch as tubular section 28 will not be subjected to peristaltic action, as will be seen hereinafter, it does not have to be constructed of the same quality as previously described section 18 and hence can be more economically provided. However, as will also be seen, in a preferred embodiment of the present invention, this particular section is utilized to monitor air bubbles within the IV fluid passing through the tubular arrangement as well as monitoring any other changes in the fluid's index of refraction. Accordingly, it is important that section 28 be constructed of a material which is at least translucent but preferably entirely transparent. In a preferred embodiment, the tube is constructed of clear polyvinyl chloride and has an inner diameter of between 0.090" and 0.180", preferably 0.118".

The otherwise free end of tubular section 28 may be suitably connected to a standard subarrangement 38 including a starter 40, a starter switch 42 and an intermediate section of tubing 44 connecting the starter and starter switch together. This particular arrangement is provided for clearing the bubbles out of the IV fluid by starting a gravity flow through the entire tubular arrangement. An end cap 46 may be provided for sealing the free end of starter 40.

In addition to the foregoing, tubular arrangement 14 may also include a second end cap 48 which is adapted for connection around the free end of luer tip 22. While this particular end cap may be conventionally provided for merely sealing the luer tip, in a preferred embodiment of the present invention, it cooperates with the luer tip to define at least one but preferably a plurality of tortuous paths between the ambient surroundings and the inside of the lower tip. The reason for these tortuous paths is to allow the introduction of a sterilization medium, for example ethylene oxide (EtO) within the tubular arrangement while the tortuous paths prevent entry of bacteria. This general procedure, that is, the utilization of a tortuous path to allow entry of a sterilization medium but prevent entry of a bacteria is convention and hence will not be discussed further.

However, the particular end cap 48 is not conventional. As illustrated, this end cap includes a longitudinally extending body which is closed at one end 50 and opened at its opposite end for receipt of luer tip 22. The cap also includes a plurality of longitudinally extending ribs 52 which extend inwardly from and which are circumferentially spaced around the inner surface of the end cap body from its open end to its closed end. These ribs are designed to tightly engage the outer surface of the luer tip so that together the tip and end cap define a plurality of tortuous spaces or passages therebetween, as best illustrated in FIG. 8 where the luer tip and end cap are shown assembled together.

Figure 1:
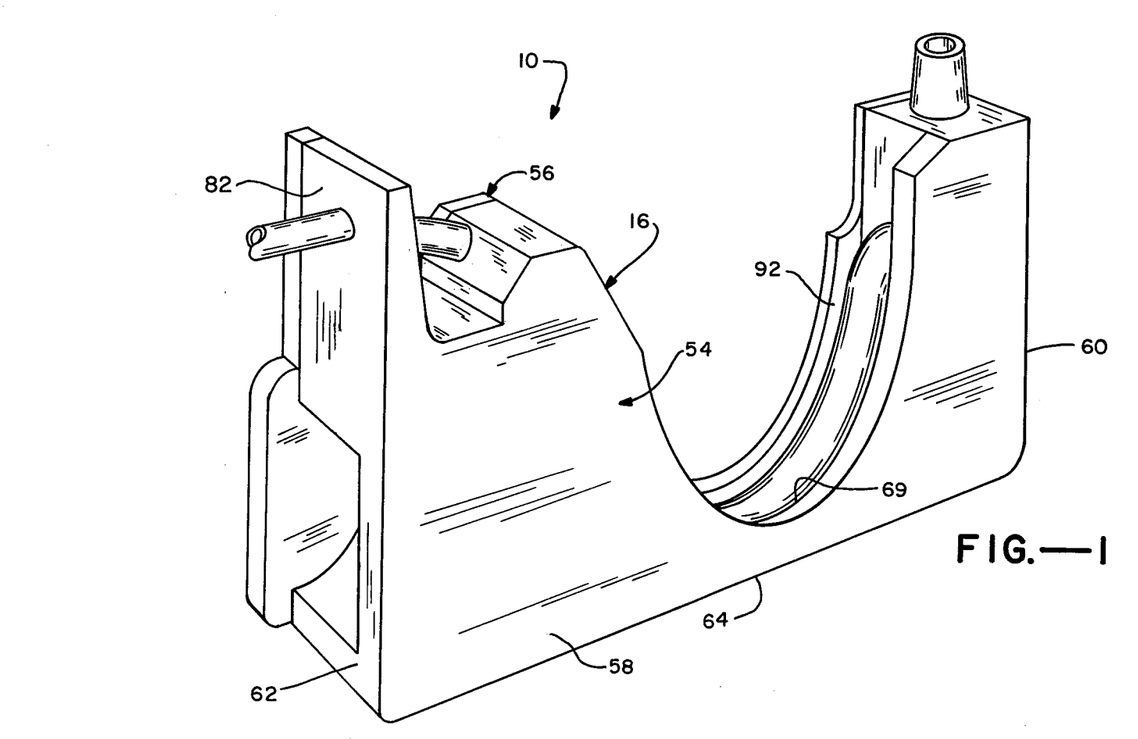
FIG. 1 is a perspective view of a disposable cassette constructed in accordance with the present invention.

Having described tubular arrangement 14, attention is now directed to cassette body 16 which is illustrated best in FIGS. 3 to 8 in conjunction with FIG. 1. This cassette body preferably consists of only two sections, a front section 54 and a back section 56. Each of these sections is injection molded or otherwise integrally formed into a single unit and is constructed of a suitable material which is sufficiently durable to function in the manner to be described. In an actual working embodiment, these sections of cassette body 16 are constructed of ABS plastic.

Figure 3:
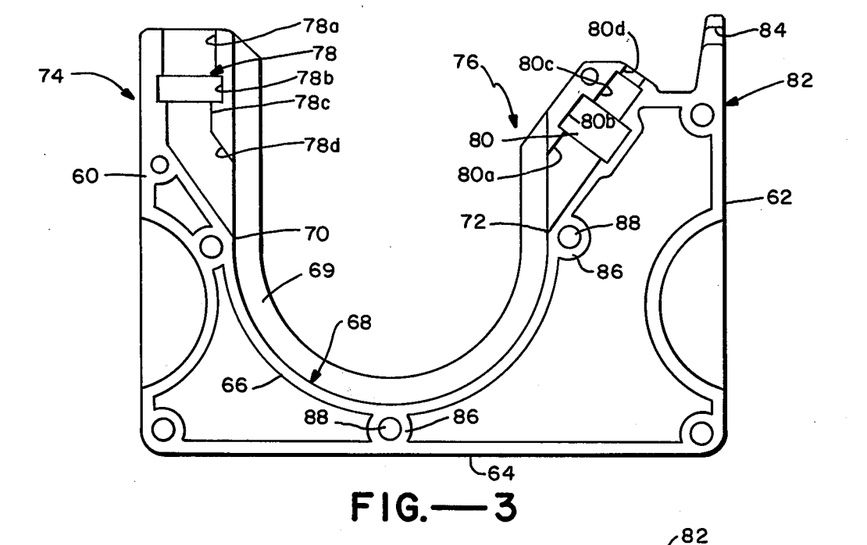
FIG. 3 is a side elevational view of one segment of the cassette of FIG. 1.
Figure 4:
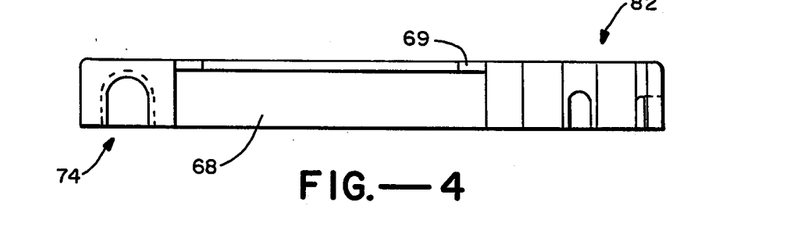
FIG. 4 is a top plan view of the cassette segment illustrated in FIG. 3.
Figure 5:
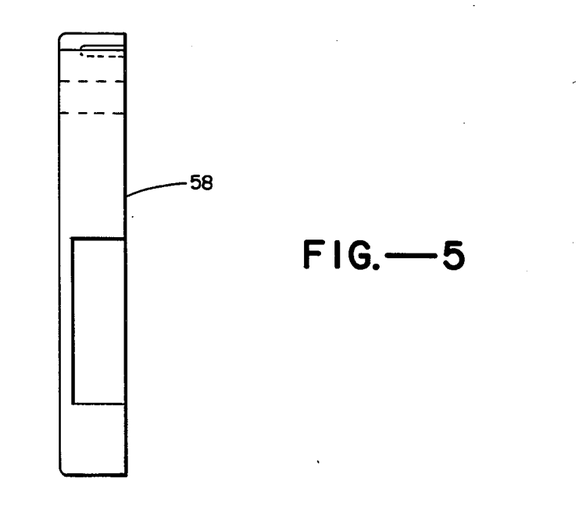
FIG. 5 is a side elevational view of the same cassette segment.
Figures 7, 8:
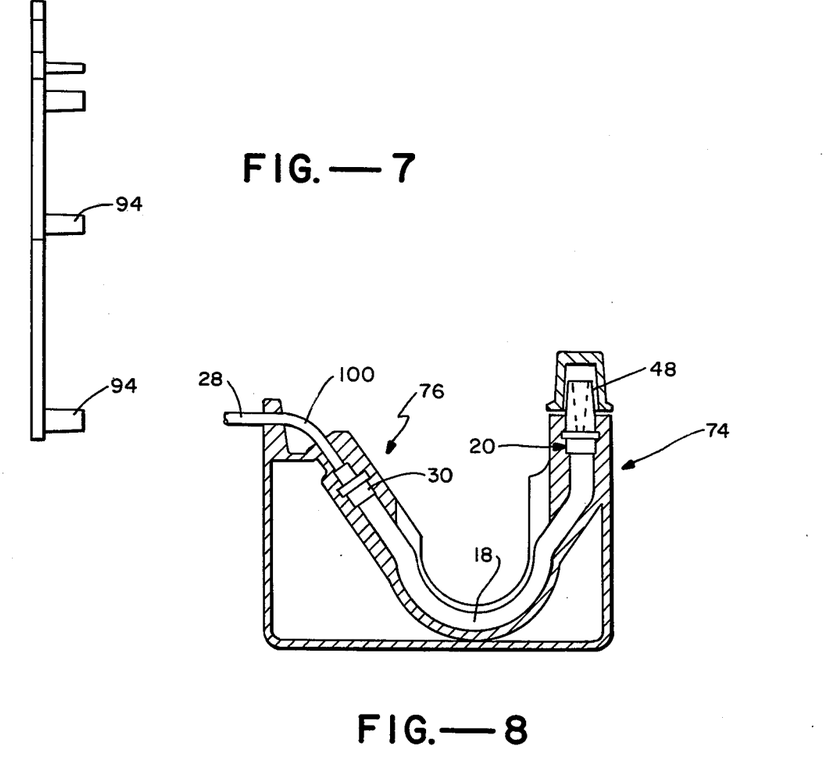
FIG. 7 is a side elevational view of this second segment.
FIG. 8 is a front sectional view of the cassette illustrating the tubular arrangement therein.

Turning to FIGS. 3, 4, and 5 in conjunction with FIG. 8, attention is specifically directed to front section 54 of cassette body 16. As illustrated in these figures, section 54 includes a continuous front plate 58 which, for purposes of description, will be used as a frame of reference. As seen in FIG. 1, this front plate extends from one end 60 of the cassette body to an opposite end 62 and from the bottom end 64 to what is clearly an irregularly shaped top end. Section 54 includes a continuous flange 66 which extends rearwardly from front plate 58 and which defines what will be referred to as an arcuate tube supporting surface 68. As best seen in FIGS. 3 and 8, this surface which faces upwardly has a predetermined radius of curvature. Actually, as illustrated, this surface defines approximately 180° of a circle, starting at one end 70 and terminating at its other end 72.

As also seen best in FIGS. 3 and 8, section 54 of cassette body 16 includes a channel defining flange arrangement 74 and a channel defining flange arrangement 76, both of which extend inwardly from front plate 58 directly above and to one side of ends 70 and 72 or surface 68, respectively. As its name implies, channel defining arrangement 74 defines open channel 78 which extends inwardly towards front plate 58 and the back end of the flange arrangement. For reasons to become apparent hereinafter, the channel is divided into four distinct subchannels 78a, 78b, 78c and 78d, all of which differ in configuration. In a similar manner, flange arrangement 76 defines an open channel 80 which, like channel 78, extends to the back side of the flange arrangement towards front plate 58 and may also be divided into four distinct channels of differing configuration, specifically channels 80a, 80b, 80c and 80d.

In addition to flange 66 and flange arrangements 74 and 76, section 54 of cassette body 16 includes a flange 82 which extends vertically upward above and rearwardly of flange arrangement 76 at the back end 62 of section 54. Actually, as seen best in FIG. 1, flange 82 is what may be referred to as an extension of the back end. This flange, as best seen in this latter figure and in FIG. 3, defines a through opening 84 which, for reasons to become apparent hereinafter, is spaced a predetermined distance from subchannel 80d of channel 80 (see FIG. 3). The cassette body also includes what will be seen hereinafter as a sidewall 69 formed by that portion of front plate 58 extending up beyond surface 68.

In addition to the various features thus described, front section 54 of cassette body 16 may include various flanges or other means necessary to its manufacture. Moreover, as illustrated best in FIG. 3, this section includes a plurality of flanges or flanged sections 86 which define openings 88. As will be seen hereinafter, these openings 88 are adapted to cooperate with connecting pins comprising part of back section 56 to connect the two sections together.

Figure 6:
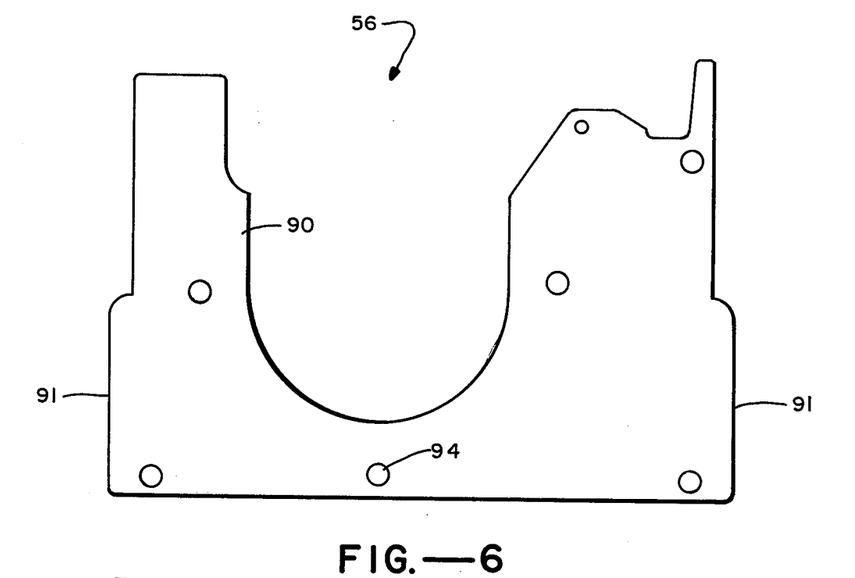
FIG. 6 is a front elevational view of a second segment of the cassette of FIG. 1.

Turning to FIGS. 6 and 7, in conjunction with FIG. 1, attention is directed to back section 56. As illustrated, this back section for the most part consists of a single plate, specifically a rearward plate 90, which is approximately the same configuration of previously recited front plate 58. This back section serves primarily two purposes. First, when it is properly assembled to the back side of front section 54, it closes previously described channels 78 and 80, that is, along the length of the channels, so that each channel actually becomes a passage which is only opened at its opposite ends. Second, this back section actually, the back plate, defines a second side wall 92 which extends up from tube supporting surface 68 directly across from previously recited side wall 69, as best seen in FIGS. 1 and 8 and side tracks 91 to be discussed hereinafter. In order to assemble back section 56 to front section 54, the back section includes a plurality of support pins which are strategically positioned for insertion into previously recited openings 88. These two sections may be connected together merely by providing a tight fit between these pins and their corresponding openings or, if it is desired or necessary, suitable adhesive or other such bonding means may be provided.

Having described cassette body 16, attention is now directed to the manner in which the cassette body supports previously described tubular arrangement 14. As illustrated best in FIG. 8, channel 78 which is defined by previously described flange arrangement 74 cooperating with back plate 90 provides means for fixedly supporting one end portion of tubular section 18 in place adjacent end 70 of surface 68. Actually, the channelled flange cooperating with the back plate not only fixedly supports one end portion of tubular section 18 in place, but also fixedly supports tip 22 in place. Moreover, in a preferred embodiment, it provides a force fit at the connection of the tubular section and tip for seal connecting the two together without the need for separate adhesive or sealant. More specifically, as seen in FIG. 8, in conjunction with FIG. 3, the subchannels 78a, 78b, 78c and 78d display a combined configuration corresponding to the configuration which results from connecting the luer tip to one end of tubular section 18. The subchannels are preferably scaled down slightly so as to provide the desired force fit, as recited above, when the front and back sections of the cassette body are assembled together.

In a similar manner, the channelled flange 76 cooperating with back plate 90 provides means for fixedly supporting an opposite end portion of tubular section 18 adjacent end 72 of surface 68. Like the various subchannels making up channel 78, the subchannels 80a, 80b, 80c and 80d of channel 80 provide a configuration which corresponds to the configuration of tubular section 18, connector 30, and on end of section 28, when these components are connected together. Moreover, these latter subchannels are also preferably scaled down slightly so that they combine with the backplate 90 to provide a force fit around the tubular sections and connector for connecting them together in a seal tight manner without the use of a separate bonding agent.

With the opposite end portions of tubular section 18 fixedly supported in place adjacent opposite ends 70 and 72 of surface 68, it can be seen, particularly in FIG. 8, that this maintains the intermediate portion of the tubular section in place across and in continuous contact with the tube supporting surface. As seen best in FIG. 1, this intermediate portion of the tubular section is positioned between the side walls 69 and 92 and is readily accessible from outside the cassette body along its entire arcuate length from point 70 to point 72.

As was stated above, tubular section 28 has one end connected with tubular section 18 within channel 78. As seen best in FIGS. 1 and 8, tubular section 28 extends out of this channel and through previously described opening 84 in up standing flange 82 and, while not shown, is ultimately connected to the starter arrangement 38, specifically to starter switch 42, as illustrated in FIG. 2. However, one point which should be noted is that one portion of tubular section 28, generally designated at 100, extends between the channel 80 and opening 84 and is maintained in this readily accessible and exposed position. The reason for this will become apparent hereinafter.

In order to complete the assembly of disposable cassette 10, the previously described end cap 48 is positioned over that portion of tip 20 which extends out beyond channel 78. As illustrated in FIG. 8, the opening of this cap does not engage channel flange 74 but is rather positioned to leave a slight gap therebetween. This gap in conjunction with the spaces defined by previously described ribs 52 define the tortuous path referred to above. In this way, the entire cassette can be subjected to a sterilization bath even after it has been entirely assembled.

Having described overall cassette 10, the various advantages attributed thereto should be quite apparent. In the first place, because the tubular arrangement is made up of a plurality of sections, only that section which is to be subjected to peristaltic action needs to be constructed of a sufficiently high quality and presumably relatively expensive material. As a result, the entire tubular arrangement nevertheless may be economical. However, this tubular section which is subjected to peristaltic action is not subject to creeping since its ends are fixedly supported in place. In this regard, a separate adhesive or other such bonding system is not required to connect these sections together which simplifies assembly and eliminates the possibility of contamination as well as reduces cost. Further, it should be quite apparent that the tubular arrangement can be rapidly and reliably assembled with the cassette body with hardly any possibility of error. Moreover, once assembled, the particular section of the tubular arrangement to be subjected to peristaltic action is fixed in place relative to the cassette body. As a result, as will be seen hereinafter, once the cassette body is fixed in position in the pump, which can be done reliably, this automatically places the tubular section in the appropriate position to be subjected to peristaltic action. As will also be seen, an important feature of this particular cassette design is that it automatically places a second section of the tubular arrangement, specifically portion 100 of tubular section 28, in a fixed position for detecting bubbles or other changes in the index of refraction of liquids passing through the arrangement.

Figure 9:
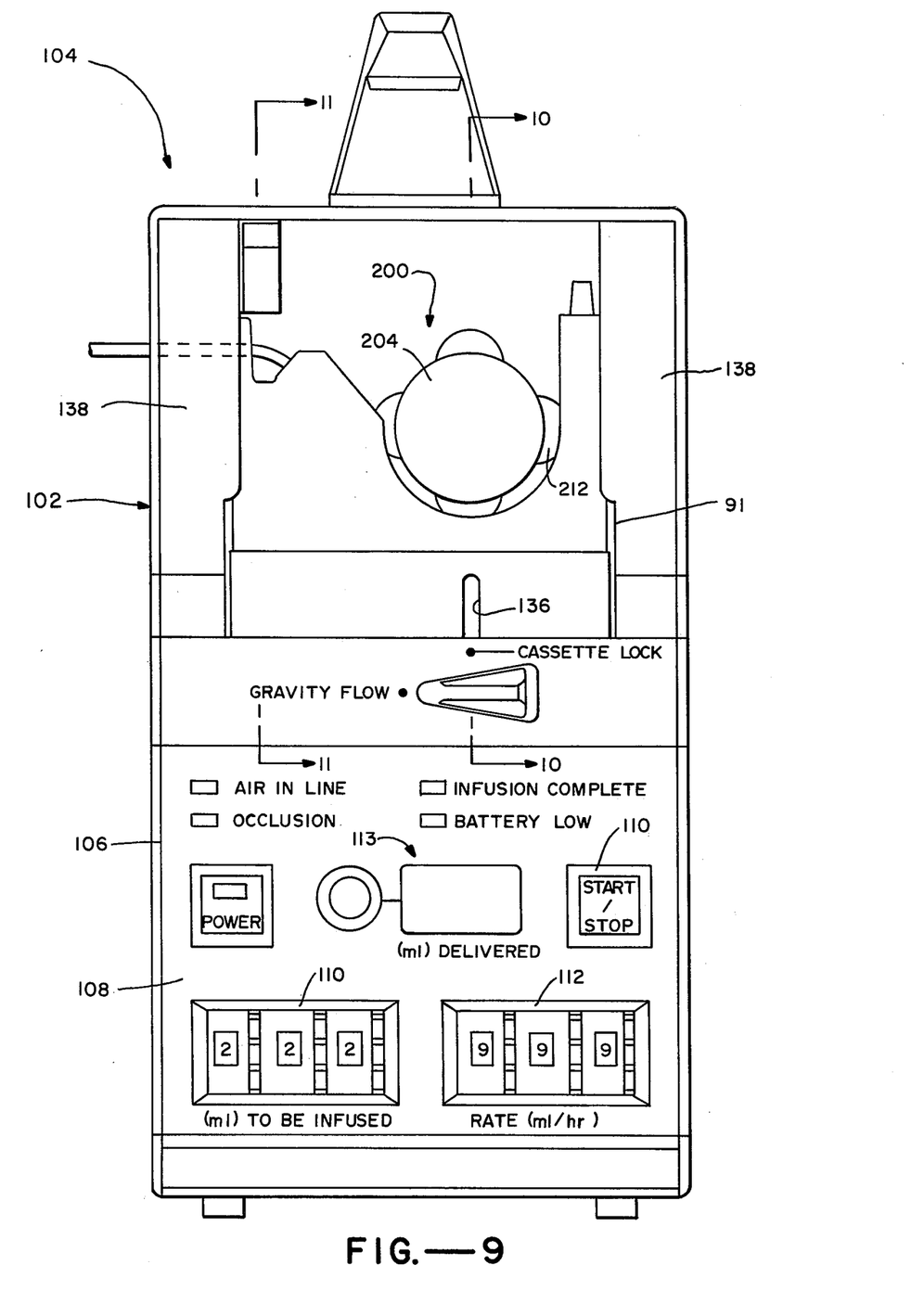
FIG. 9 is a front elevational view of an overall peristaltic pump assembly constructed in accordance with the present invention.

Having described disposable cassette 10, the way in which the cassette is assembled, and some of its advantages, attention is now directed to a pump 102 which, along with the disposable cassette 10, comprises part of an overall peristaltic infusion pump assembly 104 illustrated in FIG. 9. As will be discussed in more detail hereinafter, the pump 102 includes an overall housing 106 adapted to house and support the various components making up this pump. As illustrated in FIG. 9, this housing includes a front panel 108 displaying a number of indicators including a start/stop button 110 and two setting wheels, a three digit wheel 112 for setting the amount of IV fluid to be infused (in milliliters), and a three digit wheel 114 provided for setting the rate of fluid to be infused (in milliliters/hour). The front panel also displays a number of other indicators self-evident from FIG. 9. These latter indicators include an AIR-IN-LINE indicator, an OCCLUSION indicator, a BATTERY LOW indicator, an INFUSION COMPLETE indicator and an indicator arrangement 113 indicating the amount of fluid delivered at any point in time. These setting indicators and the start/stop button will be briefly discussed hereinafter.

In addition to the foregoing, pump 102 includes an arrangement 114 for supporting the previously described disposable cassette 10 for movement between a first inoperative position and a second spaced apart, locked operative position, as best illustrated in FIGS. 10 through 13. This pump also includes an arrangement 116 which cooperates with section 28 of previously described tubular arrangement 14 when the cassette is in its second operative position for peristaltically pumping IV fluid through the tubular arrangement. In addition to these arrangements 114 and 116, the pump includes an arrangement 118 which automatically cooperates with the previously described portion 100 of tubular section 28 of the tubular arrangement when the disposable cassette 10 is in its second operative position for automatically detecting any changes in the index of refraction of the IV fluid as the fluid passes through portion 100.

Figure 10:
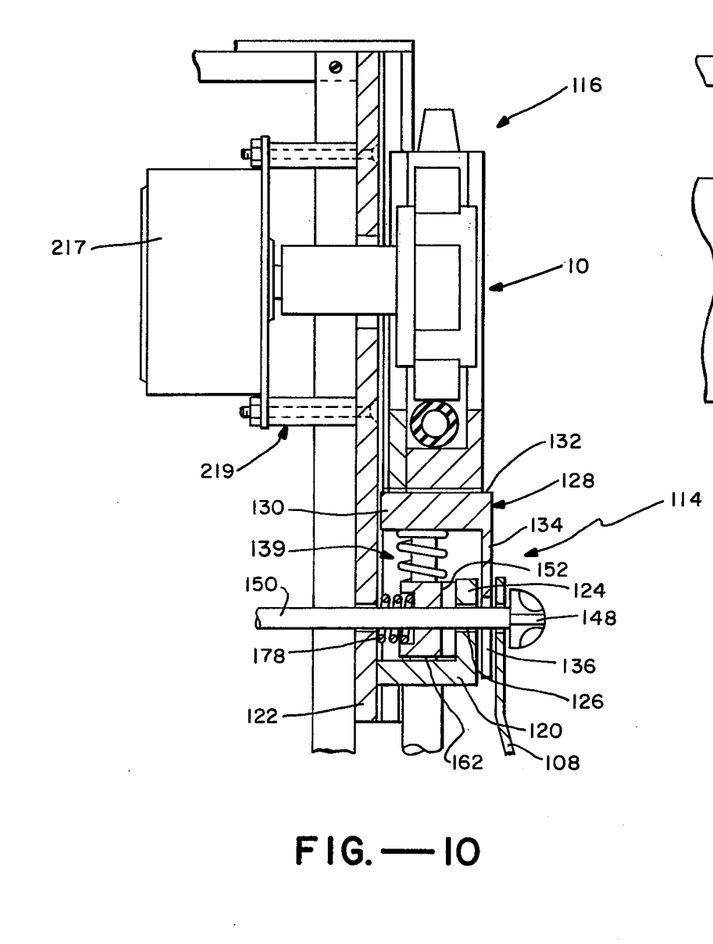
FIGS. 10 and 11 are sectional views respectively taken along lines 10—10 and 11—11 in FIG. 9.
Figure 11:
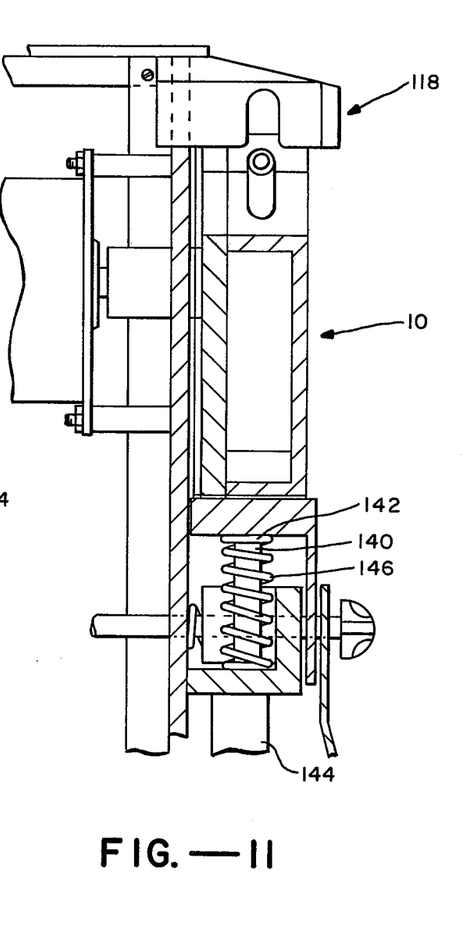

Turning to FIGS. 10 and 11, attention is specifically directed to arrangement 114. As seen in these figures, arrangement 114 includes a fixed flange 120 which is suitably mounted to the front face of a vertically extending support plate 122 comprising part of housing 106. This flange extends horizontally across the housing and includes a vertical section 124 which is spaced from support plate 122 and which, for reasons to be discussed hereinafter, includes a through passage 126.

Arrangement 114 also includes a cassette support 128 located above flange 120 directly in front of support plate 122. This cassette support includes a horizontal segment 130 which defines a horizontally extending upwardly facing cassette support surface 132 which, as will be seen hereinafter, supports the bottom 64 of the cassette. The cassette support also includes a skirt 134 depending from the front edge of segment 130 directly in front of the upstanding section 124 of flange 120 and, for reasons to become apparent hereinafter, includes a slot 136 which extends vertically upward from its bottom edge. This cassette support is mounted for limited vertical movement between two vertically extending tracks or rails 138 (see FIG. 9) which are suitably held in place to housing 106 on opposite sides of the cassette support. As will be seen below, arrangement 114 includes an overall subarrangement for moving the cassette support between a first position illustrated in FIG. 10 and a second, locked in place, vertically higher position illustrated in FIG. 12.

Cassette support 128 is supported for the movement just described by means of two support pins 140, only one of which is illustrated. These support pins include enlarged heads 142 which engage the underside of section 130 of the cassette support and extend down from the support near opposite ends thereof. These support pins extend through cooperating openings in flange 120 and are slidably mounted in fixed tubular members 144 which are fixedly connected to the underside of the flange. A compression ring 146 is positioned concentrically around each pin 140 between its associated enlarged head 142 and the bottom of its fixed tubular member 144. These compression springs maintain the pins 140 and therefore the cassette support 128 in its first lowered position illustrated in FIGS. 10 and 11.

Figure 12:
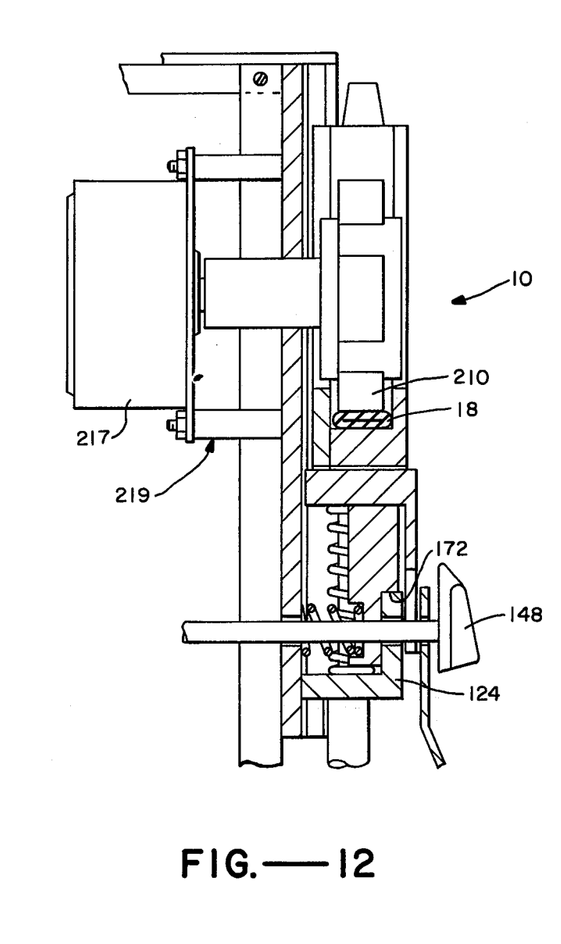
FIGS. 12 and 13 are views similar to FIGS. 10 and 11, respectively, however showing the assembly of FIG. 9 in a different operative position.
Figure 13:
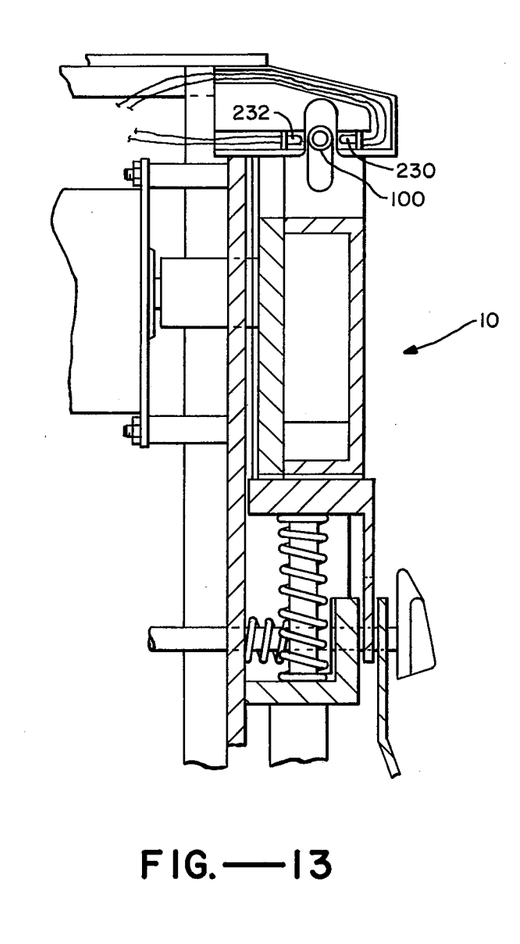

In order to move the cassette support from its biased first position to its extended second position illustrated in FIGS. 12 and 13, subarrangement 139 includes a manual switch handle 148 which is located directly in front of front panel 108 near the top edge thereof. This switch handle is fixedly connected to one end of a shaft 150 which extends through a cooperating opening in the front panel, through previously recited slot 136 in the depending skirt 134 of cassette support 28 and thereafter through previously recited passage 126 and finally through a cooperating opening in backplate 122. This shaft is mounted for rotation about its own axis between the two spring loaded pins 140. A cam member 152 is positioned around the shaft between upstanding section 124 of flange 120 and backplate 122, directly below the horizontally extending section 130 of cassette support 128.

Figure 16:
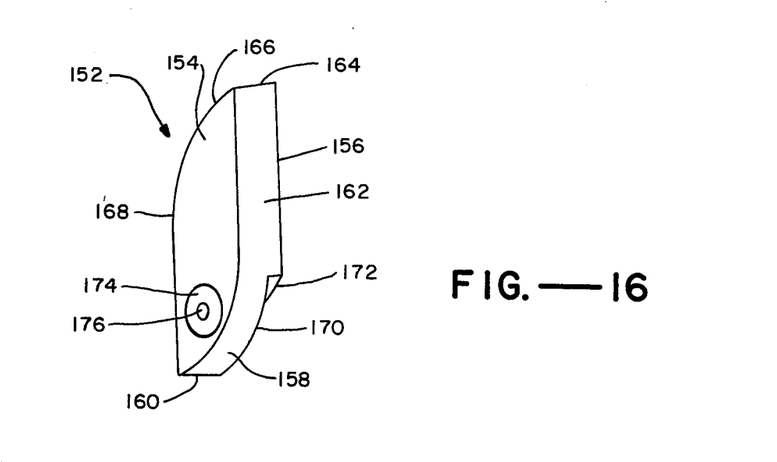

As illustrated best in FIG. 16, this cam member includes a front face 154, a back face 156, a lower curved cam surface 158 which extends from the lowermost end 160 of the cam member to a straight section 162 which in turn extends to the uppermost end 164 of the cam member. An upper curved cam surface 166 extends downward from point 164 and joins a second straight surface 168 which terminates at lowermost point 160. For reasons to follow, the cam member includes a slot 170 extending inwardly from front face 156 at the bottom of the cam member so as to define a horizontally extending, downwardly facing locking ledge 172. The opposite face of the cam member, that is back face 154, includes a counter bore 174 provided around a passage 176 through which previously recited shaft 150 passes.

Returning to FIGS. 10 through 14, it can be seen that cam member 152 is positioned around shaft 150 such that slot 170 faces upstanding section 124 of flange 120 and such that counter bore 174 faces back plate 122. The cam member is mounted around the shaft for longitudinally slidable movement relative to the shaft but fixed for rotation movement therewith. This can be readily accomplished by any conventional means such as a longitudinally extending spline arrangement (not shown). As illustrated specifically in FIGS. 10 and 11, when the cassette support 128 in its first lower position, the straight surface 162 of the cam member faces the horizontal section of the flange 120. A spring 178 is located within counter bore 174 and extends between the cam member and the back plate 122 for biasing the cam member against the vertical section 124 of flange 120 when the cam member is in the position just described. In order to move cassette support 128 to its vertically upward position, the manual switch handle 128 is rotated counter clockwise (see FIG. 9) 90°. This causes the cam member to rotate 90° from its position illustrated in FIGS. 10 and 11 to its vertically upstanding position illustrated in FIGS. 12 and 13. As this movement takes place, the cam surface 158 moves on the horizontal section of flange 120 while the cam surface 166 bears against the underside of horizontal side of section 130 of cassette support 28 causing the latter to move to its extended position. With the cam member in its vertically upstanding position, it should be noted that bottom edge 160 bears against the horizontal section of flange 120 while top edge 164 bears against the underside of section 130. It should also be noted that in this vertically upstanding position, as a result of previously described slot 170, the cam member is forced further outward so that edge 172 bears against the top edge of vertically upstanding section 124 of flange 120, as best seen in FIGS. 12 and 13. This cooperation between ledge 172 and the flange 120 prevents rotational movement of the cam member unless the switch handle 148 is moved positively inward for disengagement of the cam and hence locks the cassette support in its upper position. Also note that the surface 168 defines a sharp 90° edge with the point 160. This minimizes the possibility of the cam member overriding its 90° position before it has a chance to lock in place.

Figure 14:
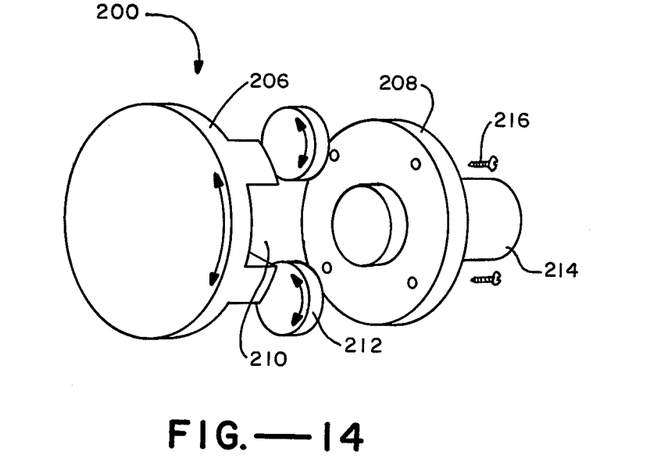
FIGS. 14–16 are perspective views of various components making up the assembly of FIG. 9.

Having described arrangement 114 including cassette support 128 and subarrangement 138 for moving the cassette support, attention is now directed to arrangement 116 which, as stated previously, cooperates with previously described tubular arrangement 14 for peristaltically pumping liquid through the tubular arrangement. Arrangement 116 includes the pump head 200 which is best illustrated in FIGS. 9 and 14. This pump head includes a cylindrical housing 204 which is preferably constructed of two integrally formed sections 206 and 208 which cooperate with one another to define a plurality of partially closed pockets 210 which are equally spaced about the circumference of the housing. In the particular pump head illustrated, four such pockets are shown. The pump head also includes an equal plurality of disc shaped, shaftless rollers 212 which are respectively positioned within corresponding pockets 210 for free rotation about their own respective axes. The housing is, in turn, fixedly mounted concentrically around one end of a central drive shaft 214. In a preferred embodiment of the present invention, the two sections 206 and 208 making up housing 204 and the shaftless rollers 212 are constructed of the same material, for example nylon, in a preferred embodiment, and are preferably integrally molded into the shapes illustrated. The two sections 206 and 208 can be held together by any suitable means, for example screws 216. The shaft 214 and the housing are connected together by fixedly connecting the shaft in a cooperating opening within section 208 by means of cement or other suitable means.

As illustrated best in FIGS. 10 to 13 in conjunction with FIG. 9, pump head 200 is located directly above surface 132 of cassette support 28. In fact, for reasons to become apparent hereinafter, the precise distance between the pump head and surface 132 is accurately fixed when the cassette support is in its upper position. Previously recited shaft 214 extends from the back end of the pump head through a cooperating opening in back plate 122, as particularly illustrated in FIGS. 10 to 13.

Arrangement 116 also includes the motor 217 which is mounted to the back side of support place 122 by any suitable means, for example, by means of bracket support 219. This motor, which may be of any suitable conventional type having a variable speed drive and energized in the conventional way, for example, electrically, is connected with the otherwise free end of shaft 214 for rotating the shaft preferably in steps and for rotating housing 204 about the axis of the shaft.

Figure 15:
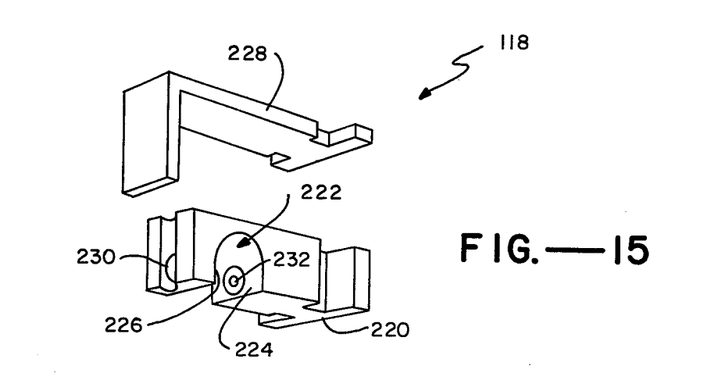

Having described arrangements 114 and 116, attention is now directed to arrangement 118 which is best illustrated in FIGS. 11 and 13 in conjunction with FIG. 15. As stated previously, this arrangement is provided for automatically detecting any changes in the index of refraction of IV fluid passing through previously recited portion 100 of tubular section 28 during operation of the overall peristaltic pump assembly. Arrangement 118 includes a housing 220 which is suitably mounted at its back end to back plate 122 (see FIG. 11) and extends forward from the back plate directly above and to one side of pump head 200 (see FIG. 9). This housing includes a transverse slot 222 which opens downward and which has a lateral extent defined by opposite sides 224 and 226. A somewhat L-shaped top cover is located over the housing.

Arrangement 118 also includes a conventional photoelectric detector arrangement including a conventional source 230 and a detector 232 which are respectively located within housing 220 on opposite sides of slot 222. This arrangement which includes conventional circuitry associated therewith (not shown) is provided for detecting bubbles or any other change in the index of refraction of the IV fluid as it passes through previously recited portion 100 of tubular arrangement 14. In this regard, as will be seen hereinafter, when the overall pump assembly is in operation, portion 100 of the tubular arrangement is automatically positioned within the slot 222.

Having described arrangements 114, 116 and 118 of pump 102, attention is now directed to the way these various arrangements of the pump cooperate with one another and with previously described disposable cassette 10 during the operation of the overall pump assembly. Let it be assumed that the assembly is initially inoperative and that the cassette support 128 is positioned in its lower inoperative position illustrated in FIGS. 10 and 11. With the cassette support in this position, the disposable cassette is placed on top of surface 132 so that its previously described guide flanges 91 (see FIG. 6) sit within cooperating grooves in rails 138, as best seen in FIG. 9. This insures that the cassette is properly positioned. In fact, unless the guide flanges are properly located, the cassette will not move up the track and hence will prevent the cassette support from moving. Once the cassette is properly positioned, the switch handle 148 is rotated 90°, as described previously, for moving the cassette support to its second position. As stated, the switch is locked in place by the interaction between cam member 152 and the top edge of section 124 of flange 120.

Turning to FIGS. 12 and 13, the cassette support and cassette is shown in this upward, operative position. Note first with respect to FIG. 12, that this causes one of the shaftless rollers 212 to completely pinch closed the intermediate portion of tubular section 18 of tubular arrangement 14 when the shaftless roller is in its lowermost position illustrated in FIG. 9. This relative positioning between the tubular section and shaftless roller, actually all these shaftless rollers as they move around axis 214, is accurately and reliably provided because of the accurately provided relative positioning between the cassette support surface 132 and the pump head. Also note that as the cassette moves to this upward operative position, portion 100 of tubular section 28 is automatically positioned within previously described slot 272 of arrangement 118 directly in line with the photoelectric detecting arrangement. With the various components described above in the various relative positions described above, the start/stop button is activated to energize motor 217 for rotating pump head 200 in the clockwise direction as viewed in FIG. 9. This causes the individual rollers to peristaltically engage tubular section 19 of the tubular arrangement for moving IV fluid through the tubular arrangement. At the same time, this fluid is continuously monitored by the photoelectric cell arrangement.

The overall peristaltic pump assembly 104 has just described without regard to the various electrical components which are necessary to its operation. For purposes of the present invention, it is to be understood that these electrical components and in fact all of the electrical circuitry which is necessary for operating the assembly may be conventional. For example, the circuit connecting the start/stop button with motor 120 may include a suitable limit switch cooperating with previously described arrangement 114 for preventing the energization of the motor until the cassette support and cassette are in their operative positions. Moreover, since the rate at which the IV fluid is to be fed through the tubular arrangement is dependent upon the speed at which the pump head is driven, suitable circuitry may be provided between the motor and rate selector 112 to vary the speed of the motor in a calibrated fashion and rate selector 112 to vary the speed of the motor in a calibrated fashion dependent upon the rate which has been set at the rate selector. Moreover, suitable circuitry may be connected between the motor and selector 210 for automatically deenergizing the motor when the selected amount of fluid has been reached. Further, suitable circuitry including the other indicators may be readily provided. A running tabulation of exactly how much fluid has been delivered at any given time during the operation may also be provided conventionally as indicated by arrangement 113. In addition, the overall assembly may include conventional means for determining whether occlusion is taking place within the line and a suitable indicator light may be provided. In this regard, one conventional way to sense occlusion is to sense a back pressure within the tubular arrangement.

As just stated, the various circuitry for operating overall assembly 104 may be conventional. However, some of this circuitry and some of the operating features may be provided in an unconventional way. For example, in copending U.S. application (Brown), Ser. No. 874,212, assigned to the assignee of the present application peristaltic infusion pump discloses a particular way in which motor 120 is energized and deenergized in a stepping type fashion. This application discloses a particular method of sensing occlusion. It also discloses a particular type of circuit arrangement for the detector associated with arrangement 118. For a description of these unconventional aspects, reference is made to the copending application. In this regard, it is however to be understood that while the various unconventional aspects disclosed in the copending application may be readily incorporated into the assembly disclosed herein, the assembly can function with all conventional circuitry and associated components as stated above.

What is claimed is:

1. A disposable cassette for use in a peristaltic pump which includes means defining a cassette support surface for supporting the cassette between a first inoperative position and a second operative position and vertically extending guide tracks located on opposite sides of said surface and extending between said inoperative and operative positions, said disposable cassette comprising:
    (a) a tubular arrangement including
        (i) a flexible first tubular section having opposite end portions and an intermediate portion joining said end portions,
        (ii) a second tubular section distinct from but joined with one end of said first section, and
        (iii) a third tubular section distinct from but joined with the other end of said first tubular section; and
    (b) a cassette body including
        (i) surface means adapted to sit on and be supported by said cassette support surface,
        (ii) an arcuate tube supporting surface located above said surface means, having a predetermined radius of curvature, and being readily accessible along its length from the top of said cassette body,
        (iii) first and second means for fixedly supporting the opposite end portions of said first tubular section in place adjacent the opposite ends of said tube supporting surface, said first and second supporting means together fixing said intermediate portion of said first tubular section in place entirely across and in continuous contact with said tube supporting surface, and
        (iv) first and second guide members on opposite sides of said surface means and extending out beyond said first and second tube supporting means, said first and second guide members being adapted to cooperate with said guide tracks whereby to guide said cassette between said inoperative and operative positions.

2. A cassette according to claim 1 wherein said first tube supporting means maintains said first and second tubular sections together at their joined ends, wherein said second tube supporting means maintains said first and third tubular sections together at their joined ends, and wherein said second tubular section includes a predetermined segment which extends away from its joined end to a predetermined support point and which is at least translucent to light, said cassette body including third means for fixedly supporting said tubular segment in place at said predetermined support point, so as to maintain said tubular segment in a fixed position between said first and third tube supporting means relative to the entire cassette body.

3. A disposable cassette for use in a peristaltic pump which includes means defining a surface for supporting the cassette between a first inoperative position and a second operative position and means for detecting any changes in the index of refraction of a liquid passing through a predetermined segment of a tube located across a predetermined detecting point, said disposable cassette comprising:
    (a) a tubular arrangement including
        (i) a flexible first tubular section having opposite end portions and an intermediate portion joining said end portions,
        (ii) a second tubular section distinct from but joined with one end of said first section, said second tubular section including a predetermined segment which extends a predetermined distance from its joined end to a predetermined support point and which is at least translucent to light and
        (iii) a third tubular section distinct from but joined with the other end of said first tubular section;
    (b) a cassette body including
        (i) surface means adapted to sit on and be supported by said cassette support surface for moving said cassette between said inoperative and operative positions,
        (ii) an arcuate tube supporting surface located above said surface means, having a predetermined radius of curvature, and being readily accessible along its length from the top of said cassette body,
        (iii) first and second means for fixedly supporting opposite ends of said first tubular section in place adjacent opposite ends of said tube supporting surface, said first and second supporting means together fixing said intermediate tube portion in place entirely across and in continuous contact with said tube supporting surface, said first means also fixedly supporting said joined end of said second tubular section, and
        (iv) third means spaced from said first means for fixedly supporting said segment in place at said predetermined support point whereby said segment is maintained in a fixed position between said first and third tubular supporting means, said segment being positioned relative to said cassette body so as to extend across said detecting point when said cassette is in said operative position, thereby allowing said detecting means comprising part of said pump to detect any changes in the index of refraction of liquid passing through said segment.

4. A disposable cassette for use in a peristaltic pump which includes means defining a cassette support surface movable between a lowered inoperative position and a raised operative position, vertically extending first and second guide tracks located on opposite sides of said surface and extending between said operative and inoperative positions and means for detecting any changes in the index of refraction of liquid passing through a tubular segment extending across a predetermined detecting point, said disposable cassette comprising:
 (a) a tubular arrangement including
  (i) a flexible first tubular section having opposite end portions and an intermediate portion joining said end portions,
  (ii) a second tubular section distinct from but joined with one end of said first section, said second tubular section including a segment which extends a predetermined distance from its joined end to a predetermined support point and which is at least translucent to light, and
  (iii) a third tubular section distinct from but joined with the other end of said first tubular section; and
 (b) a cassette body including
  (i) a bottom surface extending from one side of said cassette body to its other side, said bottom surface being adapted to sit on and be supported by said cassette support surface whereby to support said cassette between said inoperative and operative positions,
  (ii) an arcuate tube supporting surface located above said bottom surface, having a predetermined radius of curvature and being readily accessible along its length from the top of said cassette body,
  (iii) first means for fixedly supporting the joined ends of said first and second tubular sections in place adjacent one end of said tube supporting surface and second means for fixedly supporting the joined ends of said first and third tubular sections in place adjacent the other end of said tube supporting surface, said first and second supporting means together fixing the intermediate portion of said first tubular section in place entirely across and in continuous contact with said tube supporting surface,
  (iv) third means spaced from said first means adjacent one side of said cassette body for fixedly supporting said segment in place at said support point whereby said first and third means maintains said segment in fixed position, said fixed position being selected such that said segment extends across said detection point when said cassette is in said operative position, and
  (v) first and second guide members extending out on opposite sides of said cassette body, said guide members being adapted for cooperative engagement with said first and second guide tracks, respectively, for guiding said cassette between said inoperative and operative positions.

5. A cassette according to claim 4 wherein said first means maintains said first and second tubular sections in a force-fit, fluid tight manner without the use of a separate sealant and wherein said second means maintains said first and third said tubular sections in a force-fit, fluid tight manner with the use of a separate sealant.

6. A cassette according to claim 5 wherein said cassette body includes an integral front end and in integral back end which are joined together, wherein said front and back ends include a pair of upstanding walls located on opposite sides of and extending up from said tube supporting surface, whereby to prevent lateral movement of said flexible first tubular section.

7. A cassette according to claim 4 wherein said tube supporting surface defines an arc of a circle which is at most about 180°.

8. A cassette according to claim 4 wherein said cassette body consists essentially of an integrally formed front section and an integrally formed back section which are connected together to include said bottom surface, said tubular support surface, said first, second and third supporting means and first and second guide means.

9. A cassette according to claim 4 including a protective end cap removably connected to said cassette body over the unconnected end of said third tubular section, said end cap including an inner circumferential surface located concentrically around and spaced from said third tubular section, said end cap also including a plurality of ribs connected to and extending inwardly from said inner surface and engaging the outer surface of said third tubular section whereby to define a plurality of tortuous paths between the unconnected end of said third tubular section and the ambient surroundings.

10. A peristaltic pump assembly, comprising
 (A) a pump arrangement including
  (a) means including a cassette support surface for supporting a disposable cassette for movement between a first inoperative position and a second operative position,
  (b) housing means including first and second guide tracks located on opposite sides of said support surface and extending between said inoperative and operative positions, and
  (c) means cooperating with a disposable cassette located on said support surface in a predetermined way for peristaltically pumping fluid through a tubular arrangement forming part of said cassette when the latter is in said operative position; and
 (B) a disposable cassette including
  (a) a tubular arrangement including
   (i) a flexible first tubular section having opposite end portions and an intermediate portion joining said end portions,
   (ii) a second tubular section distinct from but joined with one end of said first section, and
   (iii) a third tubular section distinct from but joined with the other end of said first tubular section, and
  (b) a cassette body including
   (i) surface means adapted to sit on and be supported by said cassette support surface for supporting said cassette in said predetermined way,
   (ii) an arcuate tube supporting surface located above said surface means, having a predetermined radius of curvature, and being readily accessible along its length from the top of said cassette body,
   (iii) first and second means for fixedly supporting the opposite end portions of said first tubular section in place adjacent the opposite ends of said tube supporting surface, said first and second supporting means together fixing said intermediate portion of said first tubular section in place entirely across and in continuous contact with said tube supporting surface, and whereby said pumping means acts on said intermediate portion of said first tubular section for peristaltically pumping fluid through said tubular arrangement when said cassette is in said operative position, (iv) first and second guide members on opposite sides of said surface means and arcuate tube supporting surface and extending out beyond said first and second tube supporting means, said first and second guide members being positioned in engagement with said guide tracks whereby to guide said cassette between said inoperative and operative positions.

11. A peristaltic pump assembly, comprising:
(A) a pump arrangement including
  (a) means including a cassette support surface for supporting a disposable cassette for movement between a first inoperative position and a second operative position,
  (b) means for detecting any changes in the index of refraction of a liquid passing through a predetermined segment of a tube located across a predetermined detecting point, and
  (c) means cooperating with a disposable cassette located on said support surface in a predetermined way for peristaltically pumping fluid through a tubular arrangement forming part of said cassette when the latter is in said operative position; and
(B) a disposable cassette including
  (a) a tubular arrangement including
    (i) a flexible first tubular section having opposite end portions and an intermediate portion joining said end portions,
    (ii) a second tubular section distinct from but joined with one end of said first section, said second tubular section including a predetermined segment which extends from its joined end to a predetermined support point and which is at least translucent to light and
    (iii) a third tubular section distinct from but joined with the other end of said first tubular section,
  (b) a cassette body including
    (i) surface means adapted to sit on and be supported by said cassette support surface for supporting said cassette in said predetermined way,
    (ii) an arcuate tube supporting surface located above said surface means, having a predetermined radius of curvature, and being readily accessible along its length from the top of said cassette body,
    (iii) first and second means for fixedly supporting opposite ends of said first tubular section in place adjacent opposite ends of said tube supporting surface, said first and second supporting means together fixing said intermediate tube portion in place entirely across and in continuous contact with said tube supporting surface, whereby said pumping means acts on said intermediate portion of said first tubular section for peristaltically pumping fluid through said tubular arrangement when said cassette is in said operated position, said first means also fixedly supporting said joined end of said second tubular section, and (iv) third means spaced from said first means for fixedly supporting said segment in place at said predetermined support point whereby said segment is maintained in a fixed position between said first and third tubular supporting means, said segment being positioned relative to said cassette body so that it extends across said detecting point when said cassette is in said operative position, thereby allowing said detecting means to detect any changes in the index of refraction of liquid passing through said segment.

12. A peristaltic pump, comprising:
(A) a pump arrangement including
  (a) means including a cassette support surface for supporting a disposable cassette for movement between a first inoperative position and a second operative position,
  (b) housing means including first and second guide tracks located on opposite sides of said support surface and extending between said inoperative and operative positions,
  (c) means for detecting any changes in the index of refraction of a liquid passing through a predetermined segment of a tube located across a predetermined detecting point, and
  (d) means cooperating with a disposable cassette located on said support surface in a predetermined way for peristaltically pumping fluid through a tubular arrangement forming part of said cassette when the latter is in said operative position, and
(B) a disposable cassette including
  (a) a tubular arrangement including
    (i) a flexible first tubular section having opposite end portions and an intermediate portion joining said end portions,
    (ii) a second tubular section distinct from but joined with one end of said first section, said second tubular section including a segment which extends a predetermined distance from its joined end to a predetermined support point and which is at least translucent to light, and
    (iii) a third tubular section distinct from but joined with the other end of said first tubular section, and
  (b) a cassette body including
    (i) a bottom surface extending from one side of said cassette body to its other side, said bottom surface being adapted to sit on and be supported by said cassette support surface whereby to support said cassette in said predetermined way,
    (ii) an arcuate tube supporting surface located above said planar surface, having a predetermined radius of curvature and being readily accessible along its length from the top of said cassette body,
    (iii) first means for fixedly supporting the joined ends of said first and second tubular sections in place adjacent one end of said tube supporting surface and second means for fixedly supporting the joined ends of said first and third tubular sections in place adjacent the other end of said tube supporting surface, said first and second supporting means together fixing the intermediate portion of said first tubular section in place entirely across and in continuous contact with said tube supporting surface whereby said pumping means acts on said intermediate portion of said first tubular section for peristaltically pumping fluid through said tubular arrangement when said cassette is in said operative position, (iv) third means spaced from said first means adjacent one side of said cassette body for fixedly supporting said segment in place at said support point whereby said first and third means maintains said segment in fixed position, said fixed position being selected such that said segment extends across said detection point when said cassette is in said operative position, and (v) first and second guide members extending out on opposite sides of said cassette body, said guide members engaging said first and second guide tracks, respectively, for guiding said cassette between said inoperative and operative positions.

13. An assembly according to claim 12 wherein said peristaltic pumping means includes means for supporting a plurality of disc-shaped rollers substantially equally circumferentially spaced about an imaginary circle, each of said rollers being freely rotatable about its own axis, and means for rotating said supporting means about the axis of said circle.

14. An assembly according to claim 13 wherein said supporting means defines a plurality of partially closed pockets, one for each of said rollers, and wherein said rollers are shaftless, each of said shaftless rollers being positioned within a corresponding one of said pockets for free rotation therein.

* * * * *